(12) United States Patent
Cruz et al.

(10) Patent No.: US 10,876,753 B2
(45) Date of Patent: Dec. 29, 2020

(54) INTEGRATED SENSOR AND SERVICE PORT FOR HVAC EQUIPMENT OR HVAC SYSTEM

(71) Applicant: Watsco Ventures LLC, Coconut Grove, FL (US)

(72) Inventors: Mario A. Cruz, Miami, FL (US); Charles Peter Harland, Waterloo (CA); Christopher Todd Kirby, Melbourne (AU)

(73) Assignee: Watsco Ventures LLC, Coconut Grove, FL (US)

( * ) Notice: Subject to any disclaimer, the term of this patent is extended or adjusted under 35 U.S.C. 154(b) by 0 days.

(21) Appl. No.: 16/273,205

(22) Filed: Feb. 12, 2019

(65) Prior Publication Data

US 2019/0249892 A1    Aug. 15, 2019

Related U.S. Application Data

(60) Provisional application No. 62/629,479, filed on Feb. 12, 2018.

(51) Int. Cl.
| | |
|---|---|
| *F24F 11/50* | (2018.01) |
| *F24F 11/30* | (2018.01) |
| *C12N 5/0786* | (2010.01) |
| *C12N 5/077* | (2010.01) |
| *C12N 5/0775* | (2010.01) |
| *F24F 110/40* | (2018.01) |
| *F24F 110/10* | (2018.01) |

(52) U.S. Cl.
CPC ............ *F24F 11/30* (2018.01); *C12N 5/0645* (2013.01); *C12N 5/0656* (2013.01); *C12N 5/0663* (2013.01); *F24F 11/50* (2018.01); *C12N 2501/052* (2013.01); *F24F 2110/10* (2018.01); *F24F 2110/40* (2018.01)

(58) Field of Classification Search
CPC ........ F24F 11/30; F24F 11/50; F24F 2110/40; F24F 2110/10; C12N 5/0645; C12N 5/0656; C12N 5/0663; C12N 2501/052
See application file for complete search history.

(56) References Cited

U.S. PATENT DOCUMENTS

| | | | |
|---|---|---|---|
| 6,345,238 B1* | 2/2002 | Goodwin | G01K 7/10 257/470 |
| 2008/0289353 A1* | 11/2008 | Maruya | F25B 45/00 62/292 |
| 2011/0219790 A1* | 9/2011 | Denton | F25B 45/00 62/77 |
| 2016/0003509 A1* | 1/2016 | Pistone | G01K 13/00 29/890.031 |
| 2016/0076783 A1* | 3/2016 | Whitehead | F24F 11/30 340/870.07 |

* cited by examiner

*Primary Examiner* — Thomas C Lee
*Assistant Examiner* — Gary Collins
(74) *Attorney, Agent, or Firm* — DLA Piper LLP (US)

(57) ABSTRACT

An integrated sensor and service port for HVAC (heating, ventilating, and air conditioning) equipment or an HVAC system.

15 Claims, 4 Drawing Sheets

INTEGRATED SENSOR AND SERVICE PORT FOR HVAC EQUIPMENT OR HVAC SYSTEM

RELATED APPLICATION AND PRIORITY CLAIM

This application claims the benefit of U.S. Provisional Application No. 62/629,476, filed Feb. 12, 2018, which is hereby incorporated by reference in its entirety.

BACKGROUND

The disclosed embodiments relate to and provide an integrated sensor (e.g., pressure sensor) and service port for HVAC (heating, ventilating, and air conditioning) equipment or an HVAC system.

An HVAC system can be used to regulate the environment within an enclosed space. An HVAC system includes one or more service ports that can be used, for example, to charge the system. These ports can also be used to perform diagnostics on the system to ensure that the system is working correctly. For example, the pressure at the port can be checked to make sure it is within operational specifications. Unfortunately, to check the pressure, the port must be disconnected from the charging line so that the sensor can be attached to the port. This is undesirable as it requires additional labor and time to test the pressure. Moreover, charging cannot be performed while the pressure sensor is connected to the port.

One alternative approach is illustrated in FIG. 1. As shown, a prior art assembly 10 includes a "T" connector 12 having one part of the "T" connected to a pressure sensor 16 via a coupler 14 (e.g., by screwing them together). A communication port 18 allows communications and power for the pressure sensor. A second part of the connector 12 is attached to the service port (usually a Schrader valve). Using the "T" connector 12, the charging line can be connected at a third part of the T, while the pressure sensor can be connected to the other part of the T.

While solving the problem of having to disconnect charging while testing the pressure, this alternative has other shortcomings. For example, the various connections forming the screwed-together assembly 10 are points that can introduce leaks. Due to the rather large size of the components, the assembly is subject to physical damage as the connector 12 and sensor 16 extend from the HVAC unit and can be stepped on or bumped into by someone walking by the unit. Moreover, the assembly is not esthetically pleasing.

Accordingly, there is a need and desire for a better way to connect a pressure or other sensor (e.g., temperature sensor) to a service port of an HVAC system.

SUMMARY

The disclosed embodiments relate to and provide an integrated sensor and service port for HVAC (heating, ventilating, and air conditioning) equipment or an HVAC system. In one embodiment, the sensor may be a pressure sensor. In another embodiment, the sensor may be a temperature sensor or a combined pressure and temperature sensor with the built-in service port.

In one embodiment, an apparatus is provided. The apparatus comprises a housing, said housing having a first connection portion, a second connection portion and a sensor integrated therein, the first connection portion being configured to connect with and cooperate with a service port of heating, ventilating, and air conditioning (HVAC) equipment, the second connection portion being configured to function as the service port, and the sensor adapted to sense a characteristic of the HVAC equipment.

In another embodiment, an integrated sensor and service port device is provided. The integrated sensor and service port device comprises a brass housing, said housing having a service port opening and connection portion, a service port portion and a sensor integrated therein.

DESCRIPTION OF DRAWINGS

Like reference symbols in the various drawings indicate like elements.

DESCRIPTION

Figure 1:
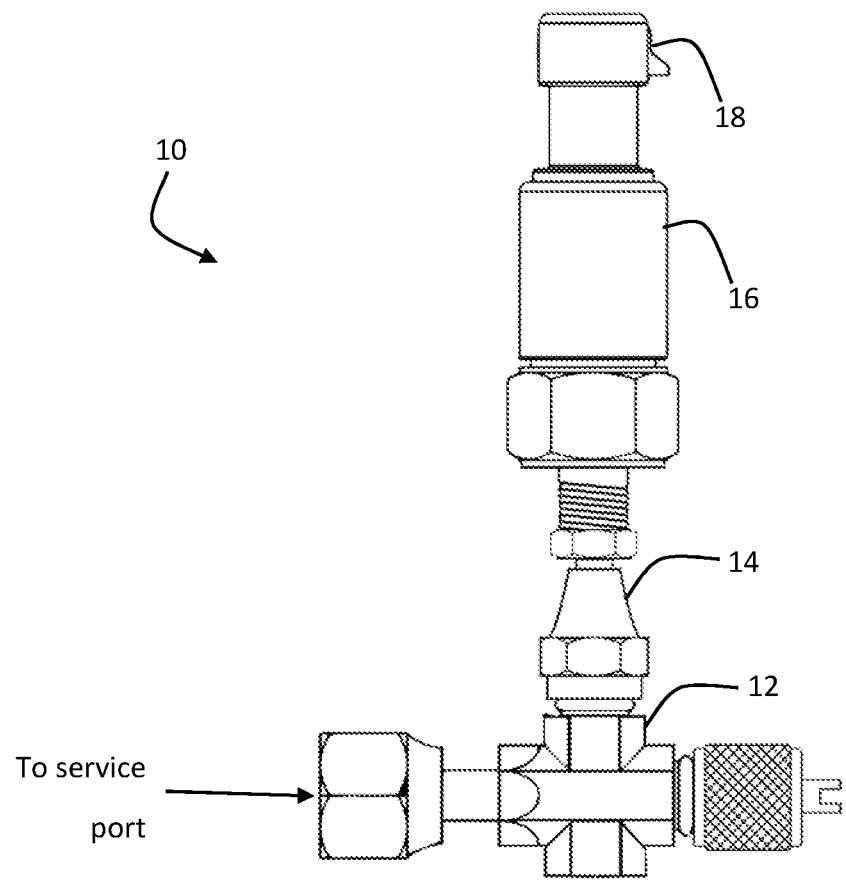
FIG. 1 illustrates a prior art assembly that may be used to measure pressure sensor on HVAC equipment or an HVAC system.
Figure 2:
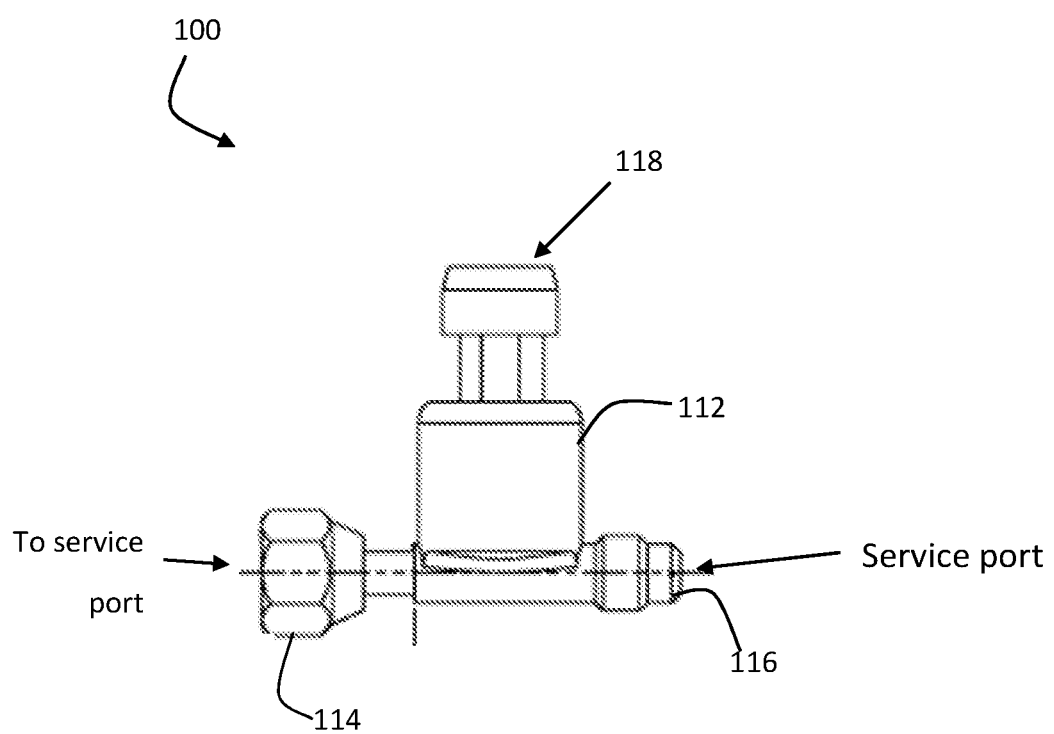
FIGS. 2-4 illustrate an example embodiment of an integrated sensor and service port in accordance with the disclosed principles.
Figure 3:
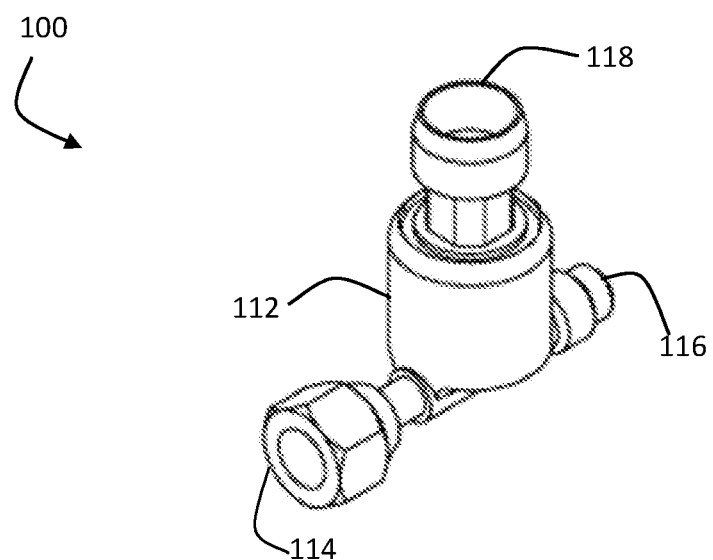

The disclosed embodiments relate to and provide an integrated sensor and service port for HVAC (heating, ventilating, and air conditioning) equipment or an HVAC system. In one embodiment, the sensor may be a pressure sensor. In another embodiment, the sensor may be a temperature sensor or a combined pressure and temperature sensor with the built-in service port.

In one or more embodiments disclosed herein, the integrated sensor and service port may comprise a pressure sensor and may be placed and used to e.g., determine: (1) pressure at the suction line service valve and/or (2) pressure at the liquid line service valve. The integrated sensor and service valve port may be connected to one or both of the Schrader valves (high side and low side).

FIGS. 2-6 illustrate an embodiment of the integrated sensor and service port 100 constructed in accordance with the disclosed principles. In the illustrated embodiment, the integrated sensor and service port 100 includes a single housing 112 into which a pressure sensor 120 (or other sensor such as e.g., a temperature sensor) may be integrated therein. In addition, a first connection portion 114 that may be a connector adapted to connect to and cooperate with an HVAC service port (e.g., Schrader valve or other type of valve) and a second connection portion 116 that may include a depressor valve 136 that may function as a service port (e.g., Schrader valve or other type of valve) may also be integrated as part of the housing 112. In one embodiment, a third connection portion 118 that may be a connector providing a mechanism to communicate the sensor's 120 reading outside of the integrated sensor and service port 100 may also be integrated as part of the housing 112.

Figure 4:
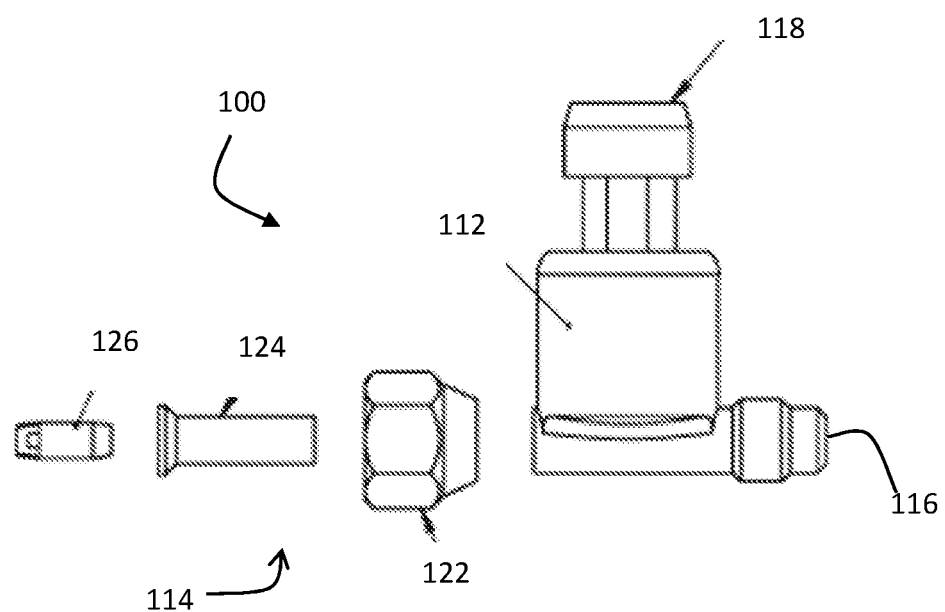

The first connection portion 114 is shown in an exploded view in FIG. 4. Referring to FIG. 4, the first connection portion 114 may include a brass tube fitting 124, flare nut 122 and a depressor fitting 126 such as e.g., a Schrader depressor fitting integrated therein. As can be appreciated, the first connection portion 114 may be connected to a service port typically used for HVAC equipment (e.g., Schrader valve or other type of valve). In the illustrated example, the first connection portion 114 includes a Schrader valve depressor 126 adapted to open the Schrader valve or other type of valve used by the equipment's service port. Thus, once the first connection portion 114 is connected to the HVAC equipment, the HVAC equipment's service port (e.g., valve) is opened by the depressor fitting 126 thus allowing the system pressure to reach the pressure sensor.

The second connection portion 116 of the integrated sensor and service port 100, due to its configuration discussed below, may be used as a service port to be connected to the charging line or other service equipment. In essence, the second connection portion 116 is an extension of the equipment's service port, allowing a charging or other line to be connected to the unit through the integrated sensor and service port 100.

Figures 5, 6:
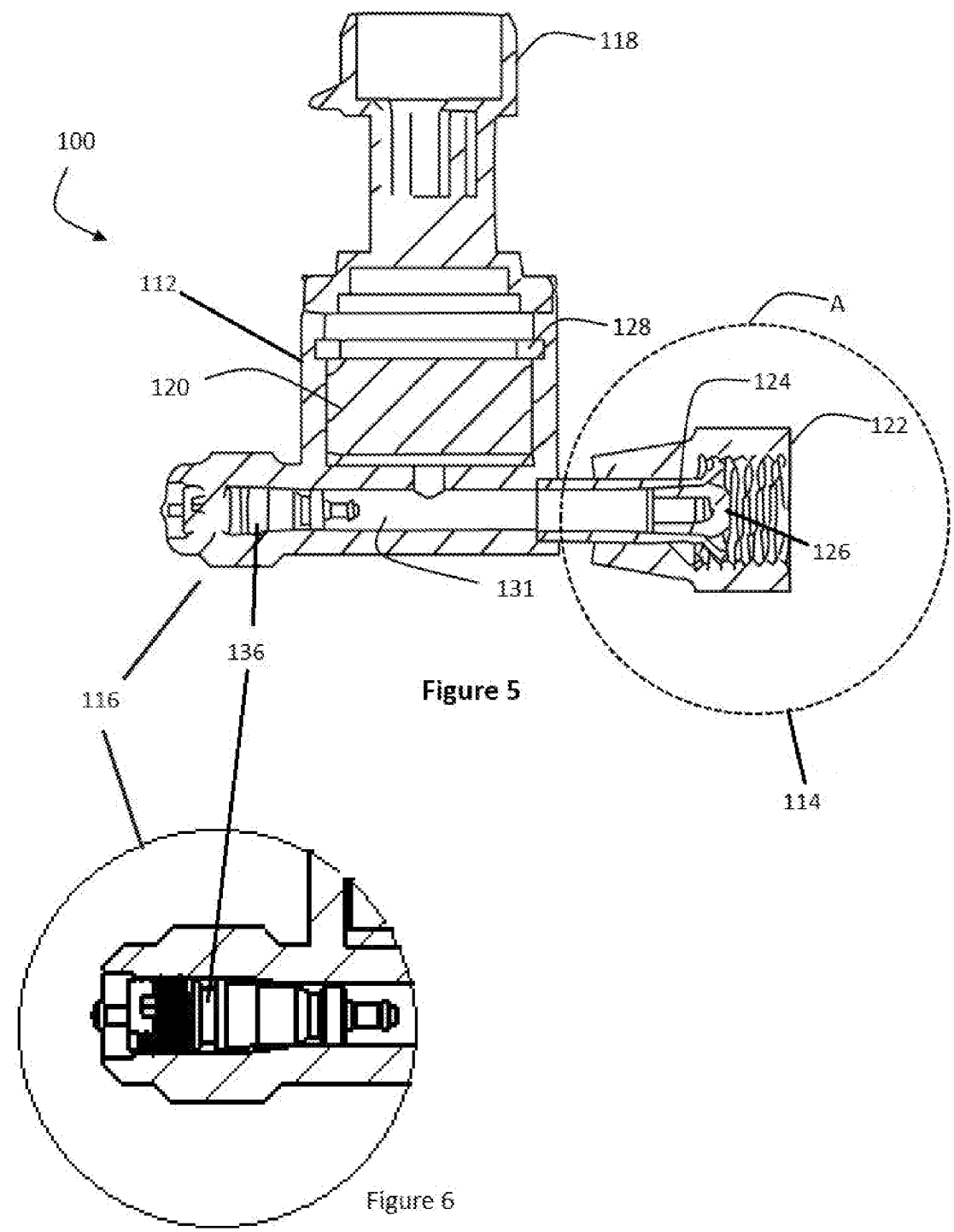
FIG. 5 illustrates a cross-sectional view of the integrated sensor and service port in accordance with the disclosed principles.
FIG. 6 illustrates an exploded view of a service port portion of the integrated sensor and service port in accordance with the disclosed principles.

As shown in the cross-sectional view of FIG. 5, the second connection portion 116 may include the threads and seal surface adapted to connect to a charging or other line typically connected to an HVAC service port. FIG. 6 illustrates an exploded view of the second connection portion 116. As can be seen, the second connection portion may include the threads and seal surface a valve 136. When connected to a charging line or other service equipment with the proper depressor, the valve pin of the valve 136 will be depressed thereby opening up the valve to allow charging or other material to enter the housing 112.

As shown in the cross-sectional view of FIG. 5, a channel 131 is formed within a tube portion of the housing 112 between the first and second connection portions 114, 116, which allows the charging or other material to enter the HVAC equipment through the first connection portion 114 of the integrated sensor and service port 100. The flared tube portion 124 may be used to connect the housing 112 to the HVAC service port.

In the illustrated embodiment, and as shown in FIG. 5, a sensor 120 is formed within the housing 112 at a point between the first and second connection portions 114, 116. The sensor 120 is also in communication with the channel 131, allowing the sensor 120 to sense a characteristic (e.g., pressure, temperature) of the HVAC unit/equipment. In one embodiment, the sensor 120 may be a pressure sensor such as e.g., a ceramic pressure sensor. In addition, the sensor 120 may be a pressure sensor capable of detecting pressure between 0 and 750 PSI (pounds per square inch). Alternatively, the sensor 120 could be a temperature sensor.

The sensor 120 is also connected to the third connection portion 118. As shown in FIG. 5, a retaining ring 128 may be located within the housing between the sensor 120 and the third connection portion 118. In one embodiment, the third connection portion 118 may be a metri pack connector allowing the reading of the sensor 120 to be sent to a monitoring system such as the system disclosed in U.S. patent application Ser. No. 15/153,950.

In one embodiment, the housing 112 may be made of brass or any other material suitable for use in an HVAC environment. The integrated sensor and service port 100 is weather proof and leak proof as all of its components are integrated into the house.

As can be appreciated, the integrated sensor and service port 100 disclosed herein has several advantages over the traditional mechanisms used to check the pressure or temperature of an HVAC unit. For example, there is no need to disconnect charging while testing the pressure or temperature. Moreover, because the components of the disclosed integrated sensor and service port 100 are integrated as one assembly, there are no connections or portions that leak. In addition, because the components of the disclosed integrated sensor and service port 100 are integrated as one assembly, it is compact and has a small size that does not lend itself to physical damage. Furthermore, the disclosed integrated sensor and service port 100 is esthetically pleasing.

The foregoing examples are provided merely for the purpose of explanation and are in no way to be construed as limiting. While reference to various embodiments is made, the words used herein are words of description and illustration, rather than words of limitation. Further, although reference to particular means, materials, and embodiments are shown, there is no limitation to the particulars disclosed herein. Rather, the embodiments extend to all functionally equivalent structures, methods, and uses, such as are within the scope of the appended claims.

Additionally, the purpose of the Abstract is to enable the patent office and the public generally, and especially the scientists, engineers and practitioners in the art who are not familiar with patent or legal terms or phraseology, to determine quickly from a cursory inspection the nature of the technical disclosure of the application. The Abstract is not intended to be limiting as to the scope of the present inventions in any way.

What is claimed is:

1. An apparatus comprising:
   a housing, said housing having a first connection portion, a second connection portion and a sensor integrated therein, the first connection portion being configured to connect with and cooperate with a service port of heating, ventilating, and air conditioning (HVAC) equipment, the second connection portion being configured to function as the service port, and the sensor adapted to sense a characteristic of the HVAC equipment,
   wherein the first connection portion, the second connection portion and the sensor are in communication with a channel formed within the housing, and the first connection portion comprises:
   a brass tube fitting coupled to the channel;
   a flare nut over the brass tube fitting; and
   a depressor fitting within the brass tube fitting.

2. The apparatus of claim 1, wherein the housing comprises brass.

3. The apparatus of claim 1, wherein the sensor is a pressure sensor.

4. The apparatus of claim 1, wherein the sensor is a temperature sensor.

5. The apparatus of claim 1, wherein the sensor is a combined pressure and temperature sensor.

6. The apparatus of claim 1, further comprising a third connection portion coupled to the sensor, the third connection portion adapted to provide a mechanism to communicate readings of the sensor outside of the apparatus.

7. The apparatus of claim 6, wherein the third connection portion is a metri connector.

8. The apparatus of claim 1, wherein the second connection portion comprises:
   a seal surface and thread to allow sealed connection of service equipment; and
   an internal valve with valve pin to allow service access to a pressurized system.

9. An integrated sensor and service port device comprising:
   a brass housing, said housing having a service port opening and connection portion, a service port portion and a sensor integrated therein, wherein the service port opening and connection portion, the service port portion and the sensor are in communication with a channel formed within the housing, and the service port opening and connection portion comprises:
a brass tube fitting coupled to the channel;
a flare nut over the brass tube fitting; and
a depressor fitting within the brass tube fitting.

10. The integrated sensor and service port device of claim 9, wherein the service port opening and connection portion is configured to connect with and cooperate with a service port of heating, ventilating, and air conditioning (HVAC) equipment, the service port portion is configured to function as the HVAC equipment service port, and the sensor is adapted to sense a characteristic of the HVAC equipment.

11. The integrated sensor and service port device of claim 9, wherein the sensor is a pressure sensor.

12. The integrated sensor and service port device of claim 9, wherein the sensor is a temperature sensor.

13. The integrated sensor and service port device of claim 9, further comprising a communication connection coupled to the sensor, the communication connection adapted to communicate readings of the sensor outside of the apparatus.

14. The integrated sensor and service port device of claim 13, wherein the communication connection is a metri connector.

15. The integrated sensor and service port device of claim 9, wherein the service port portion comprises:
a seal surface and thread to allow sealed connection of service equipment; and
an internal valve with valve pin to allow service access to a pressurized system.

* * * * *